United States Patent [19]

Brennan

[11] 4,073,780

[45] Feb. 14, 1978

[54] 4-PYRIDYLFORMIMIDOYLGLYCYL-D-PHENYLGLYCINE

[75] Inventor: Thomas M. Brennan, Old Lyme, Conn.

[73] Assignee: Pfizer Inc., New York, N.Y.

[21] Appl. No.: 771,773

[22] Filed: Feb. 24, 1977

Related U.S. Application Data

[62] Division of Ser. No. 692,323, June 3, 1976, abandoned.

[51] Int. Cl.² ............................................. C07C 103/52
[52] U.S. Cl. ............................ 260/112.5 R; 260/239.1
[58] Field of Search ................. 260/112.5 R, 295 AM

[56]  References Cited

U.S. PATENT DOCUMENTS 3,950,348   4/1976   Hirschmann et al. ........ 260/295 AM Primary Examiner—Henry R. Jiles
Assistant Examiner—Bernard Dentz
Attorney, Agent, or Firm—Connolly and Hutz

[57]  ABSTRACT

Processes for the preparation of 6-[D-2-phenyl-2-(4-pyridylformimidoylaminoacetamido)acetamido]penicillanic acid via acylation of 6-aminopenicillanic acid and derivatives thereof.

1 Claim, No Drawings

4-PYRIDYLFORMIMIDOYLGLYCYL-D-PHENYLGLYCINE

CROSS-REFERENCE TO RELATED APPLICATION

This application is a division of application Ser. No. 692,323 filed June 3, 1976 and now abandoned.

BACKGROUND OF THE INVENTION

1. Field of the Invention

Methods used to synthesize penocillins vary widely depending on the availability of starting reagents and the structure of the final product. It has now been discovered that 6-[D-2-phenyl-2-(4-pyridylformimidoylamino-acetamido)acetamido]penicillanic acid, a useful antibacterial agent, can be conveniently prepared by coupling 4-pyridylformimidoylglycyl-D-phenylglycine with 6-aminopenicillanic acid and derivatives thereof.

2. Description of the Art

U.S. Pat. No. 3,951,952 claims the product of the present invention and discloses its preparation by acylation of D-α-aminobenzylpenicillin with 4-pyridylformimidoylaminacetic acid as the acid chloride or activated ester and through the reaction of methyl 4-pyridylformimidate and 6-[D-2-phenyl-2-(aminoacetamido)acetamido]penicillanic acid.

SUMMARY OF THE INVENTION

It has been found that the penicillin of the formula:

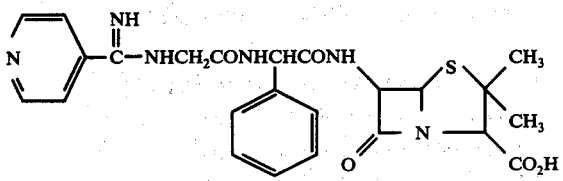

can be synthesized by contacting a 4-pyridylformimidoylglycyl-D-phenylglycine compound of the formula:

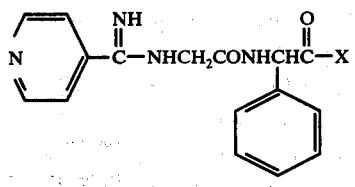

wherein X is chloro, phenoxy, 4-chlorophenoxy, 4-nitrophenoxy, phenylthio, 4-chlorophenylthio, 4-nitrophenylthio, 2-pyridylthio, N-phthalimidoxy, N-succinimdoxy, 1-benzotriazoloxy, —O—C(=NR')NHR" wherein R' and R" are each cyclohexyl or N-morpholinoethyl, or

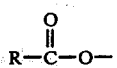

wherein R is selected from the group consisting of alkoxy having from one to four carbon atoms and t-butyl, with a 6-aminopenicillanic acid of the formula:

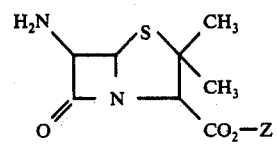

wherein Z is hydrogen or a blocking moiety selected from the group consisting of:

(a)

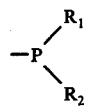

wherein $R_1$ and $R_2$ are each selected from the group consisting of alkyl having one to three carbon atoms, alkoxy having one to three carbon atoms and phenyl;

(b) 3,5-di-t-butyl-4-hydroxybenzyl;

(c) —$CH_2$—Y wherein Y is selected from the group consisting of

wherein $R_3$ is selected from the group consisting of phenyl and alkyl having one to three carbon atoms, —CN and carboalkoxy having two to four carbon atoms;

(d) —N=CH$R_4$ wherein $R_4$ is selected from the group consisting of phenyl and alkyl having one to three carbon atoms;

(e) $Sn(R_5)_3$ wherein $R_5$ is alkyl having one to four carbon atoms;

(f) $CR_6R_7R_8$ wherein $R_6$ and $R_7$ are each selected from the group consisting of hydrogen, phenyl and methyl and $R_8$ is selected from the group consisting of phenyl, 4-methoxyphenyl, 4-nitrophenyl and methyl, provided that when $R_6$ and $R_7$ are each methyl, $R_8$ is also methyl;

(g) —$CH_2CR_9R_{10}R_{11}$ wherein $R_9$ is selected from the group consisting of bromo, chloro and iodo and $R_{10}$ and $R_{11}$ are each selected from the group consisting of hydrogen, bromo, chloro and iodo; and (h) $Si(CH_3)_2R_{12}$ wherein $R_{12}$ is selected from the group consisting of methyl and 6-aminopenicillanoyloxy, in a reaction inert solvent at a pH of about 3.5–8 and reaction temperature of about 0° to −15° C., followed by removal of the blocking moiety, Z.

A preferred feature of the present invention is the acylation of the aforementioned 6-aminopenicillanic acid wherein Z is as defined, with 4-pyridylformimidoylglycyl-D-phenylglycine of the aforementioned formula wherein X is

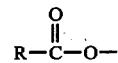

wherein R is alkoxy having from one to four carbon atoms.

A second process leading to the penicillin of the formula:

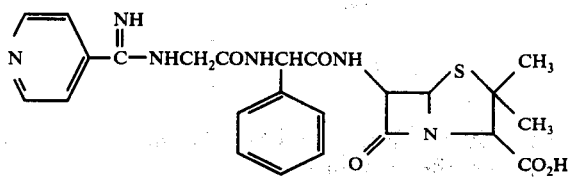

comprises contacting a 4-pyridylformimidoylglycyl-D-phenylglycine compound of the formula:

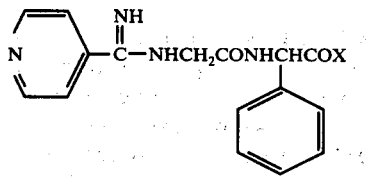

wherein X is chloro, phenoxy, 4-chlorophenoxy, 4-nitrophenoxy, phenylthio, 4-chlorophenylthio, 4-nitrophenylthio, 2-pyridylthio, N-phthalimidoxy, N-succinimdoxy, 1-benzotriazoloxy, —O—C(=NR′)NHR″ wherein R′ and R″ are each cyclohexyl or N-morpholinoethyl, or

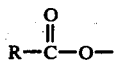

wherein R is selected from the group consisting of alkoxy having one or four carbon atoms and t-butyl, with a 6-aminopenicillanic acid derivative of the formula:

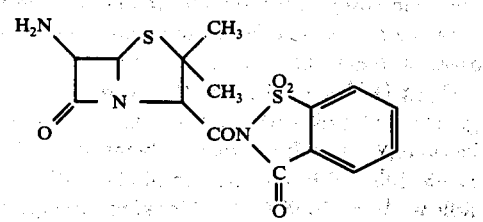

in a reaction-inert solvent, pH of 3.5–8 and reaction temperature of about −10° to −5° C., followed by aqueous hydrolysis of the saccharimide group at a pH of about 8–8.5.

A preferred feature of this second process invention comprises the acylation of the aforementioned 6-aminopenicillanic acid derivative with a 4-pyridylformimidoylglycyl-D-phenylglycine compound of the aforementioned formula wherein X is

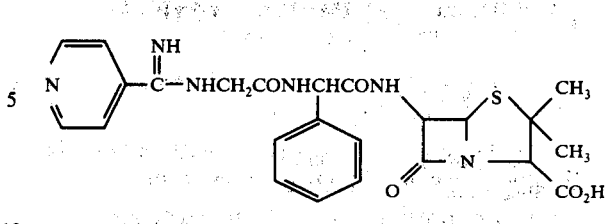

wherein R is alkoxy having from one to four carbon atoms.

Also considered within the scope of the present invention are the intermediate blocked derivatives of 6-[D-2-phenyl-2(4-pyridylformimidoylaminoacetamido)acetamido]penicillanic acid compounds wherein Z is as defined, but other than hydrogen and the side-chain acid, 4-pyridylformimidoylglycyl-D-phenylglycine, as useful intermediates.

Although acylation reactions of 6-aminopenicillanic acid are quite well known, it is particularly surprising that under the reaction conditions of the instantly claimed processes, that there is no appreciable reaction of the derivatized 4-pyridylformimidoylglycyl-D-phenylglycine with the more basic amidine portion of this side chain reactant.

In addition, there appears to be no racemization of the D-phenylglycine portion of the reactant side chain via intramolecular formation of an oxazolone derivative.

As one skilled in the art can readily appreciate, the α-carbon atom of the penicillin side chain to which the 4-pyridylformimidoylaminoacetamido moiety is attached is an asymmetric carbon allowing for the existence of two optically active isomers, the D- and L-diastereoisomers, as well as the racemate, DL form. In accord with previous findings concerning the activity of such penicillins possessing asymmetric α-carbon atoms, the compound of the present invention possessing the D-configuration is more active than that of the L-configuration and is the configuration to which the present application is restricted.

Further, it is noteworthy to mention while considering asymmetric centers, that there are several in the 6-aminopenicillanic acid nucleus, the basic building block from which the compounds of the present invention are derived. These potential additional isomers are not significant in this instance since the 6-aminopenicillanic acid employed leading to the product of this process invention is what is produced by fermentation and is consistently of one configuration.

DETAILED DESCRIPTION OF THE INVENTION

The first process reaction of the present invention is depicted in the following scheme:

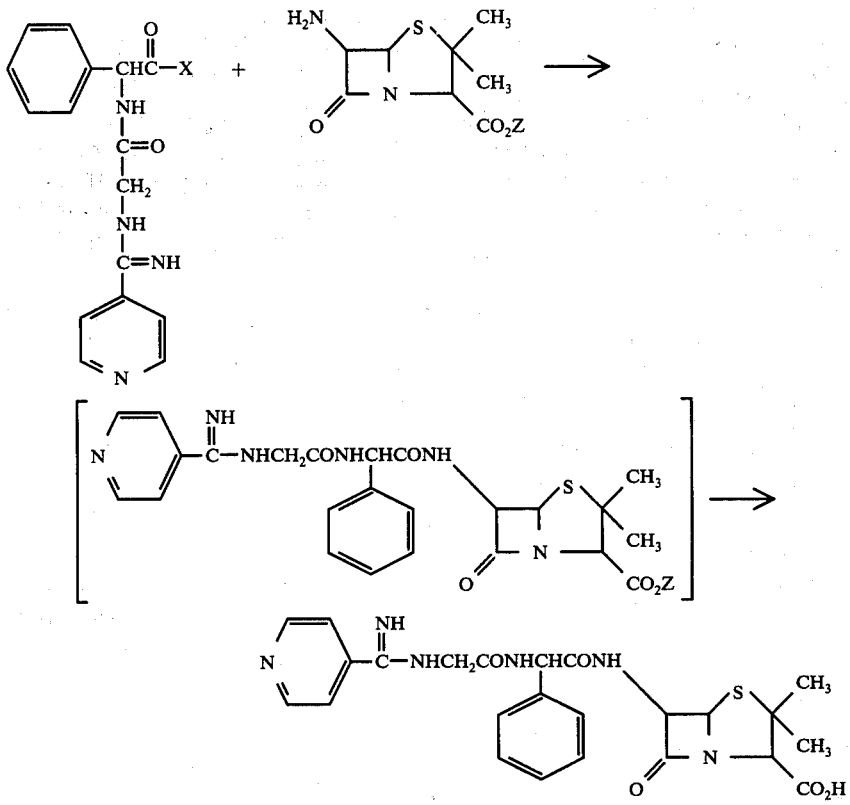

wherein X and Z are as previously defined.

In general, the acylation is carried out in a reaction-inert solvent, said solvent being one which appreciably solubilizes the reactants without reacting to any great extent with either the reactants or the products under the reaction conditions. It is preferred that these solvents be highly polar, aprotic solvents which are miscible with water and will not freeze or solidify at temperatures which represent the low end of the reaction temperature range of the claimed reaction process. Such solvents or mixtures thereof include 1-methyl-2-pyrrolidone, dimethylformamide, dimethylacetamide, dimethylsulfoxide and hexamethylphosphoramide. The preferred solvents are 1-methyl-2-pyrrolidone and dimethylformamide.

The molar ratio of reactants is not a critical factor in the claimed reaction process. The use of a slight excess of the 6-aminopenicillanic acid derivative, up to as much as ten percent, aids in the completion of the reactants and offers no serious problem in isolating the desired product in purified form.

Reaction time, too, is not critical, and is inherently dependent on concentration, reaction temperature and reactivity of the starting reagents. Under the reaction-temperature conditions of about 0° to −15° C. the reaction is usually complete in 30 minutes to 3 hours.

The preferred reaction temperature are those which allow the reaction to proceed at a practical rate without resulting in thermal degradation of the starting reagents or products of said process. Accordingly, temperatures of 0° to −15° C. are operable.

The order of the addition of the reactants is not critical. Because of the labile nature of the various derivatives of 4-pyridylformimidoylglycyl-D-phenylglycine, it is preferred that these reactants not be isolated. Consequently, it is preferred that the appropriate derivative be prepared in situ from the corresponding 4-pyridylformimidoylglycyl-D-phenylglycine. It is further preferred that the requisite derivative in an appropriate solvent of the aforementioned description be added to 6-aminopenicillanic acid deriviative in an appropriate solvent or mixture of said solvents.

As previously mentioned, the claimed process is conducted at a pH of 3.5–8. This is most conveniently carried out by employing the appropriate 4-pyridylformimidoylglycyl-D-phenylglycine derivatives as some general acid addition salt. The preferred salts include the sulfate salt, p-toluenesulfonic acid salt, the hydrobromide salt, the phosphate salt and the hydrochloride salt.

The conversion the 4-pyridylformimidoylglycyl-D-phenylglycine to the appropriate derivate suitable for acylation of the requisite 6-aminopenicillanic acid of the previously mentioned formula is carried out in a manner well-known to one skilled in the art.

In preparing those starting reagents wherein X is

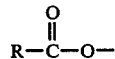

and R is alkoxy or t-butyl, 4-pyridylformimidoylglycyl-D-phenylglycine is contacted with about an equimolar amount of the appropriate acid chloride,

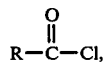

wherein R is as previously defined. The solvents suitable for the preparation of the intermediate mixed anhydrides are those which are also useful in the claimed processes. Reaction temperatures of about −15° C. are preferred, with a corresponding reaction time of 15-20 minutes. The preferred mixed anhydrides for the acylation of the 6-aminopenicillanic acid and derivatives thereof are those wherein R is ethoxy.

In synthesizing the acylating reagent wherein X is chloro, 4-pyridylformimidoylglycyl-D-phenylglycine is reacted with thionyl chloride in one or more of the solvents previously described a suitable for the claimed processes. The reaction temperatures of $-15°$ to $-20°$ are preferred, with a corresponding reaction time of 45-60 minutes.

Preparation of those acylating reagents wherein X is $-O-C(=NR')NHR''$ where R' and R'' are each cyclohexyl or N-morpholinoethyl is carried out by contacting 4-pyridylformimidoylglycyl-D-phenylglycine with the appropriate carbodiimide, $R'-N=C=N-R''$. Approximately equimolar amount of reactants are employed, said reaction being conducted in one or more of the solvents operable in the claimed processes. The reagent is generally formed at ambient temperatures requiring only a few minutes reaction time. The solution of the acylating agent is subsequently cooled to $0°$ to $-15°$ C. for the reaction with the requisite 6-aminopenicillanic acid or derivative thereof.

For the synthesis of those acylating agents wherein X is phenoxy, 4-chlorophenoxy, 4-nitrophenoxy, phenylthio, 4-chlorophenylthio, 4-nitrophenylthio, 2-pyridylthio, N-phthalimidoxy, N-succinimidoxy or 1-benzotriazoloxy, it is preferred that they be prepared through either the mixed anhydride or the intermediates wherein X is $-O-C(=NR')NHR''$ both of whose preparation has previously been discussed. In practice, after the mixed anhydride or isourea has been prepared in situ, the appropriate N-hydroxy compound, phenol or thiol is added in about equimolar amounts, resulting in the formation of the corresponding activated ester. Alternatively, all three reactants, 4-pyridylformimidoylglycyl-D-phenylglycine, the carbodiimide and the N-hydroxy compound, phenol or thiol, can be added all at the same time. The solvents preferred for the preparation of the activated ester acylating agents are the same suited to the processes of the present invention. Ambient temperatures are preferred for the formation of the acylating compound, with a reaction time of 15-20 minutes.

The aforementioned acylating agents can be used to acylate 6-aminopenicillanic acid directly (wherein Z is hydrogen) or, alternately, a derivative of 6-aminopenicillanic acid wherein Z is other than hydrogen as previously defined. These other derivatized forms of 6-aminopenicillanic acid are well-known to those skilled in the art and are relatively easy to prepare. Following the acylation of these derivatives, the blocking group, Z, is subsequently removed in a manner dictated by the nature of said Z group.

The first of these blocking groups is the phosphine ester, the preparation of which is taught in W. German application No. 2,218,209. Of those definitions for $R_1$ and $R_2$ variables for the group

methoxy is especially preferred. The preferred solvent is dimethylformamide and the preferred reaction temperature for the acylation reaction employing this 6-aminopenicillanic acid derivative is $0°$ C. Removal of the blocking group is conveniently carried out by addition of water.

A second blocking group is that wherein Z is 3,5-di-t-butyl-4-hydroxybenzyl, the preparation of this 6-aminopenicillanic acid derivative being taught in W. German application No. 2,033,493. The preferred solvent for this acylation reaction is dimethylformamide. The reaction temperature is $-10°$ C. with a corresponding reaction time of 20-30 minutes. Following the acylation of the 6-aminopenicillanic acid derivative, the blocking group is removed by aqueous hydrolysis at pH 8.0.

The third type of blocking moiety suitable for 6-aminopenicillanic acid are those wherein Z is $CH_2-Y$ where Y is as previously defined. The preparation of these 6-aminopenicillanic acid derivatives is taught in Acta. Chem. Scand., 21, 2210 (1967). It is preferred that these derivatives be acylated in the preferred reaction-inert solvent of dimethylformamide at a reaction temperature of $-10°$ C. for a reaction time of about 30 minutes. Removal of the blocking group is done by treatment with iodide ion, thiocyanate or mercaptan ion or an amine; the preferred removal is with potassium thiophenoxide. The preferred Y for this blocking group

wherein $R_3$ is phenyl.

The fourth type of blocking moiety is that wherein Z is $-N=CHR_4$ wherein $R_4$ is as previously defined. The synthesis of these 6-aminopenicillanic intermediates is taught in J. Chem. Soc., 1917 (1971c). Dimethylformamide is the preferred solvent for the acylation of these derivatives, employing a reaction temperature of $0°$ C. and reaction time of 30-35 minutes. At the completion of the acylation reaction the blocking moiety can be removed by treatment with a nucleophile such as mercaptide, thiocyanate or iodide ion. The preferred removal is with sodium iodide. The preferred $R_4$ for this blocking moiety is phenyl.

The fifth type of blocking group employed in the claimed process is that where Z is $Sn(R_5)_3$, said 6-aminopenicillanic acid derivatives having been prepared according to the method as reported in Acta. Chem. Scand., 22, 367 (1968). Acylation of these blocked 6-aminopenicillanic acid derivatives is preferably carried out in dimethylformamide as the reaction solvent, employing a reaction temperature of $-5°$ C. and a corresponding reaction time of 30-45 minutes. The blocking group can be conveniently removed using a mercaptide or thiocyanate ion as the nucleophile; the preferred reagent for removal is potassium thiophenoxide. The preferred $R_5$ for this blocking moiety is n-butyl.

The sixth useful blocking group, Z, on the 6-aminopenicillanic acid reagent is $-CR_6R_7R_8$ wherein $R_6$, $R_7$ and $R_8$ are as previously defined. These derivatives are prepared by the method as taught in J. Med. Chem., 11, 929 (1968). Especially preferred in the process are those intermediates wherein $R_6$ and $R_7$ are each hydrogen and $R_8$ is p-methoxyphenyl. The acylation reaction is conveniently carried out in the preferred solvent, dimethylformamide, at a reaction temperature of $-10°$ C. and reaction time of 30-45 minutes. When the reaction is complete, the blocking moiety can be removed by hydrolysis with hydrofluoric acid or by catalytic hydrogenation using palladium on charcoal. Both these latter methods of removal are preferred.

The seventh type of blocking group useful in the claimed process is that wherein Z is —CH$_2$CR$_9$R$_{10}$R$_{11}$ where R$_9$, R$_{10}$ and R$_{11}$ are as indicated. These 6-aminopenicillanic acid intermediates are prepared by the procedure of West German Application No. 1,937,962. The preferred solvent for the acylation of these derivatives is dimethylformamide, the preferred reaction temperature being $-5°$ C. with a reaction time of 30-60 minutes. The blocking group, wherein the preferred definition of R$_9$, R$_{10}$ and R$_{11}$ are each chloro, is removed by electrolytic reduction.

The eighth type of blocking moiety is that wherein Z is —Si(CH$_3$)$_2$R$_{12}$ wherein R$_{12}$ is as previously indicated; the preferred R$_{12}$ is CH$_3$. Acylation of these blocked 6-aminopenicillanic acid derivatives is conveniently carried out in dimethylformamide, with a reaction temperature of $-10°$ C. and reaction time of 60-90 minutes. The blocking group is easily removed by simple water hydrolysis. Such blocked derivatives of 6-aminopenicillanic acid are prepared according to the procedures in Ann., 673, 166(1964).

As previously mentioned, the claimed process can also be applied to the acylation of the unblocked 6-aminopenicillanic acid wherein z is hydrogen. The preferred solvent for this acylation is 1-methyl-2-pyrrolidone and the reaction temperature should be maintained at about $-10°$ C. Employing these conditions, the reaction time is about 15-20 minutes.

In all the aforementioned acylation reactions the desired product, 6-[D-2-phenyl-2-(4-pyridylformimidoylaminoacetamido)acetamido]penicillanic acid, is conveniently isolated by the precipitation of the zwitterion with the addition of methanol to the reaction mixture after the blocking group has been removed. As one skilled in the art can readily appreciate, very low concentration (g./ml.) of the product in the reaction mixture makes isolation by addition of a precipitating solvent very inefficient. Accordingly, it is preferred that when a dilute solution of 1-2% of the product in the reaction mixture are employed, that the mixture be concentrated such that higher concentrations are obtained. In general, a concentration of the product in the reaction mixture of 10% or better result in excellent recovery by methanol precipitation. Obviously, when Z is hydrogen no removal prior to isolation is necessary. Such precipitation of the product should be carried out as near as possible to its isoelectric point of pH 5.5. Depending on the pH of the solution after deblocking, hydrochloric acid or aqueous sodium hydroxide solution can be added to adjust the pH to said isoelectric point.

A second process of the present invention, useful for the synthesis of 6-[D-2-phenyl-2-(4-pyridylformimidoylaminoacetamido)acetamido]penicillanic acid, is depicted in the following scheme:

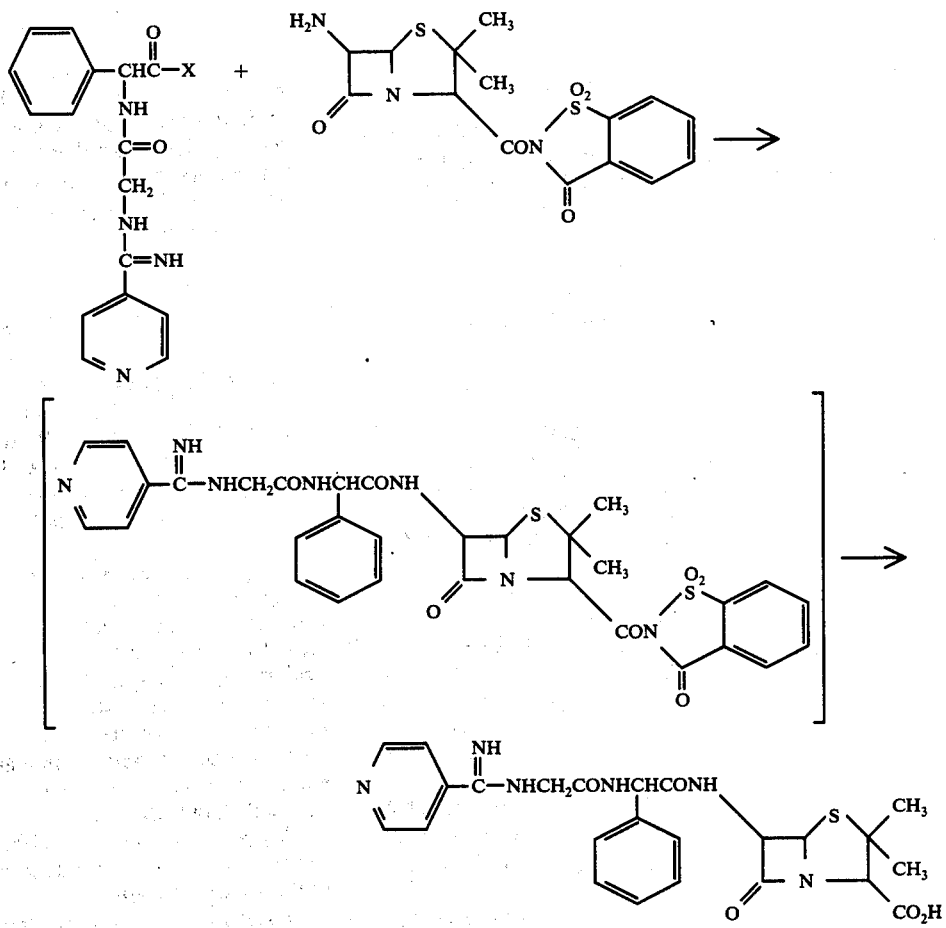

wherein X is as previously defined.

The acylation is carried out, as indicated in the first process, in a reaction-inert solvent, said solvent being one which appreciably solubilizes the reactants without reacting to any great extent with either the reactants or the products under the reaction conditions. Again, it is preferred that these solvents be highly polar, aprotic solvents which are miscible with water and will not freeze or solidify at temperatures which represent the low end of the reaction temperature range of the claimed reaction process. Such solvents or mixtures thereof include 1-methyl-2-pyrrolidone, dimethylformamide, dimethylacetamide, dimethylsulfoxide and hex- The starting 6-aminopenicillanic acid saccharimide derivative is synthesized by the procedure of British Pat. No. 1,281,952.

Also included within the scope of the present invention as useful intermediates are the intermediate blocked derivatives of 6-[D-2-phenyl-2-(4-pyridylformimidoylaminoacetamido)acetamido]penicillanic acid of the formulae:

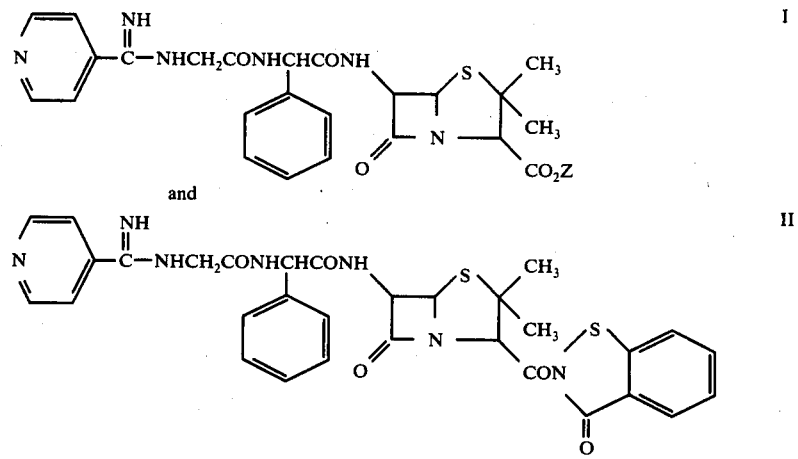

amethylphosphoramide. The preferred solvent is dimethylformamide.

The molar ratio of reactants is not a critical factor in the claimed reaction process. The use of a slight excess of the 6-aminopenicillanic acid saccharimide derivative, up to as much as ten percent, aids in the completion of the reactants and offers no serious problem in isolating the desired product in purified form.

Reaction time, too, is not critical, and is inherently dependent on concentration, reaction temperature and reactivity of the starting reagents. Under the reaction-temperature conditions of about −10° to −5° C., the reaction is usually complete in 30–60 minutes.

The preferred reaction temperatures are those which allow the reaction to proceed at a practical rate without resulting in thermal degradation of the starting reagents or products of said process. Accordingly, temperatures of −10° to −5° C. are operable, with a preferred temperature of −5° C.

The order of the addition of the reactants is not critical. As previously discussed, because of the labile nature of the various derivatives of 4-pyridylformimidoylglycyl-D-phenylglycine, it is preferred that these reactants not be isolated. Consequently, it is preferred that the requisite derivative be prepared in situ from 4-pyridylformimidoylglycyl-D-phenylglycine. In addition, it is preferred that the requisite derivative in an appropriate solvent of the aforementioned description be added to the 6-aminopenicillanic acid saccharimide derivative in an appropriate solvent or mixture of solvents.

Following the completion of the acylation reaction, the blocking saccharimide group is removed by adjusting the pH of the reaction mixture to 8–8.5 with a suitable inorganic base and allowing the mixture to stir at room temperature for about 3–4 hours.

Isolation of the desired product is achieved as in the first process, by precipitation of the zwitterion at the isolated point of 5.5. Aqueous hydrochloric acid is used to lower the pH to this preferred pH.

wherein Z is as previously described, but other than hydrogen, and the side chain acid, 4-pyridylformimidoylglycyl-D-phenylglycine.

Among these useful intermediates which are especially preferred are those related to I where Z is —$PR_1$ and $R_2$ where $R_1$ and $R_2$ are each methoxy; Z is 3,5-di-t-butyl-4-hydroxybenzyl; Z is

where $R_3$ is phenyl; Z is —N=$CHR_4$ where $R_4$ is phenyl; Z is $Sn(R_5)_3$ where $R_5$ is n-butyl; Z is —$CR_6R_7R_8$ where $R_6$ and $R_7$ are each hydrogen and $R_8$ is p-methoxybenzyl; Z is —$CH_2CR_9R_{10}R_{11}$ wherein $R_9$, $R_{10}$ and $R_{11}$ are each chloro; and Z is —$Si(CH_3)_2R_{12}$ where $R_{12}$ is $CH_3$. Also preferred is the compound of formula II.

The penicillin described herein exhibits in vitro activity against a wide variety of micro-organisms, including both gram-positive and gram-negative bacteria. Its useful activity can readily be demonstrated by in vitro tests against various organisms in a brain-heart infusion medium by the usual twofold serial dilution technique. The in vitro activity of the herein described compound renders it useful for topical application in the form of ointments, creams and the like, or for sterilization purposes, e.g., sick-room utensils.

This penicillin is also an effective antibacterial agent in vivo in animals, including man, via the parenteral route of administration.

Obviously, the physician will ultimately determine the dosage which will be most suitable for a particular individual person, and it will vary with the age, weight and response of the particular patient as well as with the nature and extent of the symptoms and the nature of the bacterial infection being treated.

Having full regard for the foregoing factors, it is considered that an effective daily parenteral dose of 25–100 mg./kg. per day, with a preferred range of about 20-75 mg./kg. per day, will effectively alleviate the symptoms of the infection. These values are illustrative, and there may, of course, be individual cases where higher or lower dose ranges are merited.

The following examples are provided solely for the purpose of illustration.

EXAMPLE 1

6-[D-2-Phenyl-2-(4-pyridylformimidoylaminoacetamido)acetamido]penicillanic Acid

A. Chloroacetyl-D-Phenylglycine

The pH of a mixture of 120.8 g. of D-phenylglycine in 800 ml. of water is adjusted to 12 with 6N aqueous sodium hydroxide, and the resulting clear solution layered over with 400 ml. of benzene and cooled to 5° C. Chloroacetyl chloride (277.2 g.) is added slowly over 45 min. to the vigorously stirred solution. The temperature is maintained at 0°-3° C. with cooling and the pH at 12.0 by the periodic addition of 6N aqueous hydroxide solution during the addition period. Subsequent to the addition, the reaction mixture is stirred for an additional hour at 5° C. and is then acidified to pH 2 with 50% aqueous sulfuric acid. The reaction mixture is extracted with ethyl acetate (2 × 500 ml.) and the combined extracts dried over magnesium sulfate and evaporated under reduced pressure to dryness. The residue is triturated with 400 ml. of cold diethyl ether, filtered and dried, giving 130 g. (72% yield) of the desired product.

B. 4-Pyridylformimidoylglycyl-D-phenylglycine

A solution of chloroacetyl-D-phenylglycine in 500 ml. of concentrated aqueous ammonium hydroxide (37%) is allowed to stir overnight at room temperature. The solution is evaporated in vacuo to dryness, and the residue slurried in acetone. The precipitate is filtered, washed with acetone and repulped in methanol (200 ml.) at 45° C. for 1 hour. The curde glycyl-D-phenylglycine product is filtered and dried, 20.4 g.

To a suspension of the crude dipeptide in 100 ml. of water and 100 ml. of dimethylformamide is added sufficient 6N aqueous sodium hydroxide to raise the pH to 9.4. To the resulting solution is added 20 g. of methyl 4-pyridylformimidate in 100 ml. of dimethylformamide, and the reaction mixture allowed to stir at room temperature for 2 hrs. The reaction is acidified to pH 5.7 with 12N hydrochloric acid and washed with 200 ml. of methylene chloride. The aqueous solution is concentrated in vacuo to 100 ml. and diluted with 350 ml. of methanol. After stirring for 1 hour, the precipitate is filtered and redissolved in 150 ml. of dimethylformamide. Some insolubles are removed by filtration and the filtrate diluted with 350 ml. of methanol. After stirring for an hour, the precipitate is filtered and dried to give 24.14 g. (85% yield) of the desired product.

C. 6-[D-2-Phenyl-2-(4-pyridylformimidoylaminoacetamido)acetamido]penicillanic acid To a solution of 10.32 g. of 4-pyridylformimidoylglycyl-D-phenylglycine in 125 ml. of dimethylformamide at −15° C. is added 3.56 g. of ethyl chloroformate, and the resulting solution, after stirring at −15° C. for 15 min., is cooled to −20° C.

To a suspension of 7.13 g. of 6-aminopenicillanic acid in 60 ml. of water neutralized to pH 7.8 with a dilute aqueous sodium hydroxide solution and cooled to 5° C. is added 40 ml. dimethylformamide. The solution is then cooled to −10° C. and the solution of the dipeptide mixed anhydride is added slowly over a 5 min. period. Cooling is continued during the addition such that the temperature remains at −10°±1° C. The reaction mixture is allowed to stir at −10° C. for an additional 15 min., and is then allowed to warm to room temperature. The clear solution is concentrated in vacuo at 35° C. to approximately 135 ml., and is diluted with 400 ml. of methanol. After stirring overnight, the resulting precipitate is filtered, washed with methanol and dried, 12.97 g. (74% yield).

The product is indistinguishable via infrared and nuclear magnetic resonance spectroscopy from that prepared by the processes of U.S. Pat. No. 3,951,952.

Similar results are obtained when methyl, i-propyl and n-butyl chloroformates are employed in place of ethyl chloroformate.

EXAMPLE 2

To a solution of 1.25 g. of 4-pyridylformimidoylglycyl-D-phenylglycine in 25 ml. of dry dimethylformamide cooled to −15° C. is added 485 mg. of pivaloyl chloride. After allowing the reaction mixture to stir for 15 min. at −10° C., 950 mg. of 6-aminopenicillanic acid in 20 ml. of water adjusted to pH 7.8 and at a temperature of 5° C. is added to the dimethylformamide solution. The temperature, which rose to 7° C. during the addition, was held at 0° C. for 15 min. and then allowed to warm to room temperature over a 30 min. period.

High-pressure-liquid-chromotography of an aliquot indicates a yield of 1.17 g. (58% yield) of the desired product, 6-[D-2-phenyl-2-(4-pyridylformimidoylaminoacetamido)acetamido]penicillanic acid, identical with the product of Example 1.

EXAMPLE 3

A suspension of 2.16 g. of 6-aminopenicillanic acid in 40 ml. of methylene chloride is treated with 1.08 g. of triethylamine and allowed to stir at room temperature until a clear solution results. The solution is cooled to 0° C. and 1.28 g. of dimethoxychlorophosphine is added.

After stirring for 15 min. a solution of the mixed anhydride, formed by adding 1.18 g. of ethyl chloroformate to 3.12 g. of 4-pyridylformimidoylglycyl-D-phenylglycine in 40 ml. of dimethylformamide cooled to −15° C., is added over a 5 minute period while the reaction temperature is maintained at 0° to −5° C. Stirring is continued for an additional 30 min. followed by dilution of the reaction with 20 ml. of water. The hydrolyzed reaction mixture is stirred for 20 min. and the aqueous layer separated and treated with 200 ml. of methanol. The product, which crystallizes from the aqueous-methanol solution, is identical to that isolated in Example 1.

EXAMPLE 4

The following pairs of mixed anhydrides and phosphine penicillanic acid esters prepared by the procedures of Examples 1 and 2, and 3, respectively, provide the desired product, 6-[D-2-phenyl-2-(4-pyridylformimidoylaminoacetamido)acetamido]penicillanic acid:

4-pyridylformimidoylglycyl-D-phenylglycine methoxyformic anhydride and di-n-propylphosphinyl 4-aminopenicillanate;

4-pyridylformimidoylglycyl-D-phenylglycine i-propoxyformic anhydride and diphenylphosphinyl 4-aminopenicillanate;

4-pyridylformimidoylglycyl-D-phenylglycine n-butoxyformic anhydride and dimethoxyphosphinyl 4-aminopenicillanate;

4-pyridylformimidoylglycyl-D-phenylglycine pivalic anhydride and dimethoxyphosphinyl 4-aminopenicillanate;

4-pyridylformimidoylglycyl-D-phenylglycine ethoxyformic anhydride and di-n-propylphosphinyl 4-aminopenicillanate; and 4-pyridylformimidoylglycyl-D-phenylglycine pivalic anhydride and diphenylphosphinyl 4-aminopenicillanate;

EXAMPLE 5

A. 4-Pyridylformimidoylglycyl-D-phenylglycine ethoxyformic anhydride

In a manner similar to Example 4, a solution of 3.12 g. of 4-pyridylformimidoylglycyl-D-phenylglycine in 40 ml. of dimethylformamide cooled to −15° C. is treated with 1.18 g. of ethyl chloroformate. After stirring for 15 min. at −15° C. the solution is further cooled to −50° C.

B. 6-[D-2-Phenyl-2(4-pyridylformimidoylaminoacetamido)acetamido]penicillanic acid A solution of 5 g. of 6-aminopenicillanic acid, 3′,5′-di-t-butyl-4′-hydroxybenzyl ester in 50 ml. of N-methyl-2-pyrrolidone at −10° C. is treated with a dimethylformamide solution of 4-pyridylformimidoylglycyl-D-phenylglycine ethoxyformic anhydride (Example 5A). After stirring 20 min. at −10° to −15° C. the cooling bath is removed and a solution of 1.82 g. of sodium 2-ethylhexanoate in 20 ml. of methanol is added. Stirring is continued for 3 hrs. at room temperature followed by the addition of 200 ml. of methanol. The product, which crystallizes, is identical with that isolated from Example 1.

EXAMPLE 6

The following mixed anhydrides, when reacted with 6-aminopenicillanic acid, 3′,5′-di-t-butyl-4-hydroxybenzyl ester according to the procedure of Example 5B, provides the desired product, 6-[D-2-phenyl-2-(4-pyridylformimidoylaminoacetamido)acetamido]penicillanic acid:

4-pyridylformimidoylglycyl-D-phenylglycine methoxyformic anhydride;

4-pyridylformimidoylglycyl-D-phenylglycine i-propoxyformic anhydride;

4-pyridylformimidoylglycyl-D-phenylglycine n-butoxyformic anhydride; and 4-pyridylformimidoylglycyl-D-phenylglycine pivalic anhydride.

EXAMPLE 7

To an ice-cooled suspension of 4.9 g. of 6-aminopenicillanic acid, phenacyl ester benzenesulfonic acid salt in 50 ml. of dimethylformamide is added 1.1 g. of triethylamine. To the resulting solution, which is cooled to −5° to −10° C., is added slowly the mixed anhydride as prepared in Example 5A. After stirring in the cold for 30 min., the reaction mixture is diluted with 100 ml. of water and extracted with ethyl acetate. The organic extracts are combined, washed with water, dried over sodium sulfate and concentrated to dryness. The residue is dissolved in 40 ml. of dimethylformamide and treated with a solution of 1.2 g. of potassium thiophenoxide in 10 ml. of dimethylformamide. After stirring at room temperature for 1 hour the pH of the solution is adjusted to 5.5 by the addition of 2N hydrochloric acid followed by the addition of 200 ml. of methanol. The desired product which slowly crystallizes from the solution is identical in all respects to the 6-[D-2-phenyl-2-(4-pyridylformimidoylaminoacetamido)acetamido]penicillanic acid formed in previous examples.

EXAMPLE 8

6-[D-2-Phenyl-2-(4-pyridylformimidoylaminoacetamido)acetamido]penicillanic acid, identical with that prepared in preceeding examples, is synthesized by following the procedure of Example 7 employing the following pairs of reactants:

4-pyridylformimidoylglycyl-D-phenylglycine methoxyformic anhydride and 6-aminopenicillanic acid, acetonyl ester;

4-pyridylformimidoylglycyl-D-phenylglycine n-butoxyformic anhydride and 6-aminopenicillanic acid, cyanomethyl ester;

4-pyridylformimidoylglycyl-D-phenylglycine ethoxyformic anhydride and 6-aminopenicillanic acid, methoxycarbomethyl ester;

4-pyridylformimidoylglycyl-D-phenylglycine pivalic anhydride and 4-aminopenicillanic acid, phenacyl ester;

4-pyridylformimidoylglycyl-D-phenylglycine i-propoxyformic anhydride and 4-aminopenicillanic acid, propionylmethyl ester;

4-pyridylformimidoylglycyl-D-phenylglycine ethoxyformic anhydride and 4-aminopenicillanic acid, i-butyrylmethyl ester;

4-pyridylformimidoylglycyl-D-phenylglycine pivalic anhydride and 4-aminopenicillanic acid, n-propoxycarbomethyl ester;

4-pyridylformimidoylglycyl-D-phenylglycine n-butoxyformic anhydride and 4-aminopenicillanic acid, cyanomethyl ester; and 4-pyridylformimidoylglycyl-D-phenylglycine pivalic anhydride and 4-aminopenicillanic acid, acetonyl ester.

EXAMPLE 9

A solution of 4.9 g. of O-(6-aminopenicillanoyl)benzaldehyde oxime p-toluenesulfonic acid salt in 50 ml. of N-methyl-2-pyrrolidone cooled to 0° C. is treated with 1.1 g. of triethylamine and then 4-pyridylformimidoylglycyl-D-phenylglycine ethoxyformic anhydride in 40 ml. of the same solvent prepared according to the procedures of Example 5A. After stirring in the cold for 30 min. the solution is warmed to room temperature and 1.5 g. of sodium iodide in 20 ml. of acetone is added. Stirring is continued for 3 hrs. followed by dilution of the solution with 200 ml. of methanol and adjustment of the pH to 5.5 with 2N hydrochloric acid. The precipitated product, when filtered, is identical to 6-[D-2-phenyl-2-(4-pyridylformimidoylaminoacetamido)-penicillanic acid prepared in Example 1.

EXAMPLE 10

In a manner similar to Example 9, the following 6-aminopenicillanic acid ester and anhydrides are reacted to give 6-[D-2-phenyl-2-(4-pyridylformimidoylaminoacetamido)acetamido]penicillanic acid, identical to that prepared in preceeding examples:

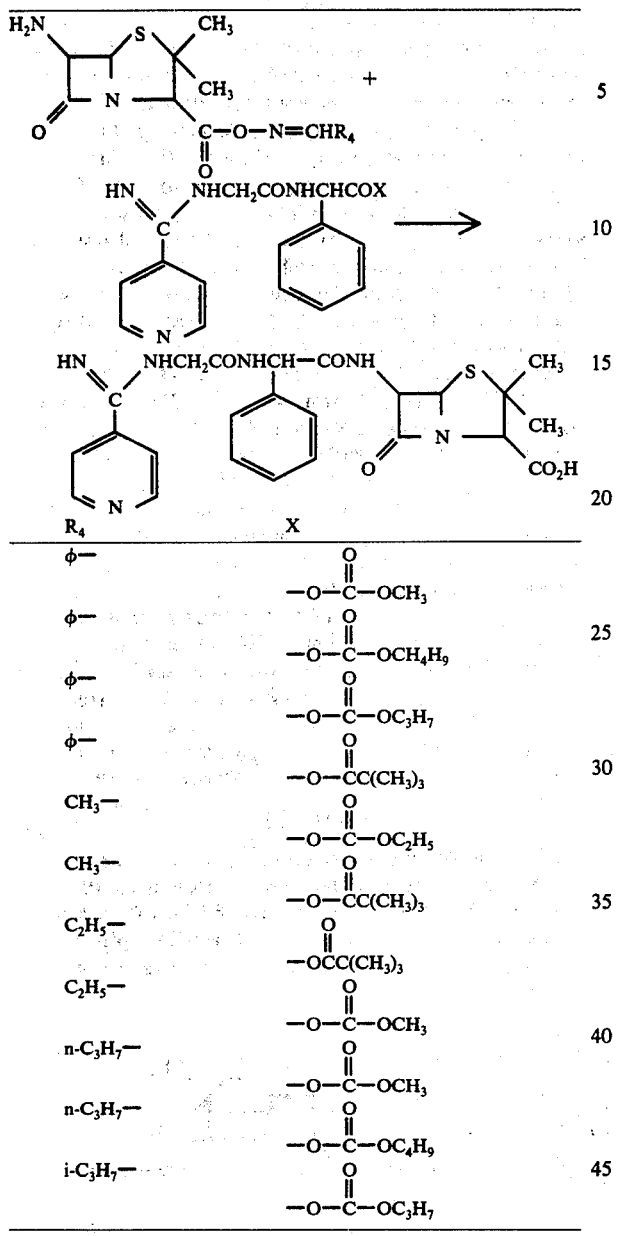

EXAMPLE 11

To a solution of 5.0 g. of tri-n-butyltin 6-aminopenicillinate in 50 ml. of dimethylacetamide cooled to −5° C. is added a solution of 4-pyridylformimidoylglycyl-D-phenylglycine ethoxyformic anhydride as prepared in Example 5A. After stirring in the cold for 30 min., the reaction solution is allowed to warm to room temperature and is subsequently treated with 1.62 g. of potassium thiophenoxide. After stirring for 30 min. at room temperature, the solids are filtered and the filtrate diluted with 200 ml. of methanol. The crystallized material, after filtration, provided the desired 6-[D-2-phenyl-2-(4-pyridylformimidoylaminoacetamido)acetamido]penicillanic acid product, identical with that formed in Example 1.

EXAMPLE 12

Following the procedure of Example 11, and starting with indicated pairs of appropriate reactants, 6-[D-2-phenyl-2-(4-pyridylformimidoylaminoacetamido)acetamido]penicillanic acid, identical with that formed in Example 1, is prepared:

4-pyridylformimidoylglycyl-D-phenylglycine ethoxyformic anhydride and trimethyltin 6-aminopenicillinate;

4-pyridylformimidoylglycyl-D-phenylglycine pivalic anhydride and triethyltin 6-aminopenicillinate;

4-pyridylformimidoylglycyl-D-phenylglycine methoxyformic anhydride and tri-n-propyltin 6-aminopenicillinate;

4-pyridylformimidoylglycyl-D-phenylglycine n-butoxyformic anhydride and tri-i-butyltin 6-aminopenicillinate;

4-pyridylformimidoylglycyl-D-phenylglycine i-propoxyformic anhydride and tri-i-propyltin 6-aminopenicillinate;

4-pyridylformimidoylglycyl-D-phenylglycine pivalic anhydride and tri-s-butyltin 6-aminopenicillinate; and 4-pyridylformimidoylglycyl-D-phenylglycine ethoxyformic anhydride and tri-n-propyltin 6-aminopenicillinate.

EXAMPLE 13

A solution of 4-pyridylformimidoylglycyl-D-phenylglycine ethoxyformic anhydride, prepared according to the procedure of Example 5A, is added over a 5 min. period to a solution of 3.3 g. of 6-aminopenicillanic acid, p-methoxybenzyl ester in 40 ml. of dimethylformamide cooled to −10° C. Stirring is continued in the cold for 30 min. followed by the addition of 200 ml. of water. The pH is subsequently adjusted to 6.0 and the solution washed twice with methyl i-butyl ketone. The pH of the aqueous phase is then lowered to 2.0 and extracted (3x) with a 5% dioctyl sulfosuccinic acid in methyl i-butyl ketone. The organic phase is separated, washed with dilute hydrochloric acid and layered with water, the pH of which is adjusted to 6.0. The aqueous layer is separated and lyophylized to give the crude intermediate p-methoxybenzyl ester of 6-[D-2-phenyl-2-(4-pyridylformimidoylaminoacetamido)acetamido]penicillanic acid hydrochloride salt.

The crude ester hydrochloride salt is added to 100 ml. of acetone containing 10 g. of anhydrous hydrogen fluoride and the mixture allowed to stir at 0° C. for 1 hour. Most of the solvent is removed at 0° C. under reduced pressure and the residue dissolved in 25 ml. of water. The pH of the aqueous solution is raised to 5.5 with a 2N sodium hydroxide solution and treated with decolorizing charcoal. The filtrate is treated with 25 ml. of dimethylformamide and 200 ml. of methanol. The product which crystallizes is identical to 6-[D-2-phenyl-2-(4-pyridylformimidoylaminoacetamido)acetamido]penicillanic acid, the product of Example 1.

EXAMPLE 14

In a manner similar to Example 13, the following 6-aminopenicillanic acid ester and anhydrides are reacted to give 6-[D-2-phenyl-2-(4-pyridylformimidoylaminoacetamido)acetamido]penicillanic acid, identical to that prepared in Example 1:

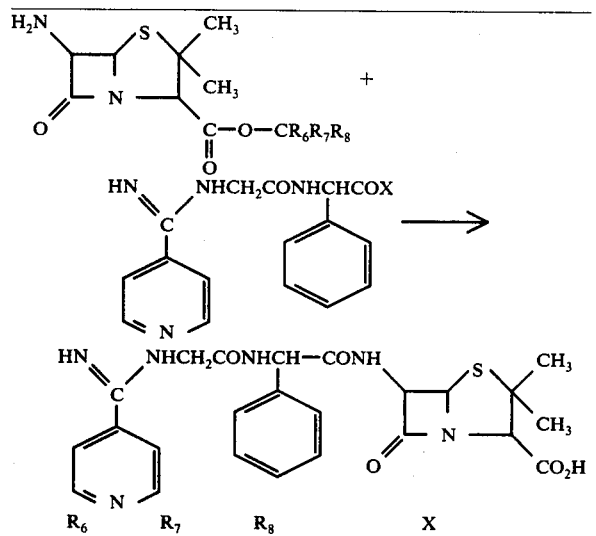

| R_6 | R_7 | R_8 | X |
|---|---|---|---|
| CH_3— | CH_3— | CH_3— | —O—C(=O)—OC_2H_5 |
| CH_3— | CH_3— | CH_3— | —O—C(=O)C(CH_3)_3 |
| H— | CH_3— | 4-CH_3OC_6H_4— | —O—C(=O)—OCH_3 |
| H— | CH_3— | 4-CH_3OC_6H_4— | —O—C(=O)—OC_3H_7 |
| CH_3— | CH_3— | 4-CH_3OC_6H_4— | —O—C(=O)—OC_2H_5 |
| CH_3— | CH_3— | 4-CH_3OC_6H_4— | —O—C(=O)—OC_4H_9 |
| H— | H— | 4-NO_2C_6H_4— | —O—C(=O)—OC_2H_5 |
| H— | C_6H_5— | C_6H_5— | —O—C(=O)—OC_2H_5 |
| H— | C_6H_5— | C_6H_5— | —O—C(=O)C(CH_3)_3 |
| C_6H_5— | C_6H_5— | C_6H_5— | —O—C(=O)C(CH_3)_3 |
| C_6H_5— | C_6H_5— | C_6H_5— | —O—C(=O)—OCH_3 |
| C_6H_5— | C_6H_5— | 4-CH_3OC_6H_4— | —O—C(=O)—OC_3H_7 |
| C_6H_5— | C_6H_5— | 4-NO_2C_6H_4— | —O—C(=O)C(CH_3)_3 |
| H— | CH_3— | 4-NO_2C_6H_4— | —O—C(=O)—OC_2H_5 |
| H— | CH_3— | 4-NO_2C_6H_4— | —O—C(=O)—OCH_3 |

EXAMPLE 15

A solution of 3.48 g. of 6-aminopenicillanic acid, $\beta,\beta,\beta$-trichloroethyl ester in 40 ml. of dimethylformamide cooled to $-10°$ C. is treated dropwise over a 5 min. period with a dimethylformamide solution of 4-pyridylformimidoylglycyl-D-phenylglycine ethoxyformic anhydride prepared according to the procedure of Example 5A. After stirring for 30 min. at $-5°$ to $-10°$ C., the reaction mixture is diluted with 20 ml. of water and poured into the cathode side of a divided cell preparative electrolysis apparatus. The anode compartment is filled with 0.1M sodium chloride solution containing 1 g. of hydrazine hydrochloride. Plate graphite anode and cathode electrodes (2.5 × 4 cm) were introduced, and the cathode adjusted to $-1.5$ vt (vs. S.C.E.) using a Princeton Applied Electronics Model 373 potentiostat. Constant potential electrolysis is carried out until the current has fallen to 5% of its original value. During this time period the pH of the cathode compartment is maintained at 5.5 and the interior temperature at 20° C. A total of 650 milliamps is consumed during the electrolysis period of 3 hrs.

The contents of the cathode compartment is decanted and the solution treated with 200 ml. of methanol. The solution, on standing, deposits a crystalline material identical with product from Example 1.

Similarly, reduction results were obtained by treating the crude trichloroethyl ester intermediate in solution with sufficient acid to provide a pH of 1.0, followed by addition of 1 g. of zinc dust at 0° C. for 1 hr.

EXAMPLE 16

Using the electrolytic reduction procedure of Example 15, the following esters are employed as starting materials for the synthesis of 6-[D-2-phenyl-2-(4-pyridylformimidoylaminoacetamido)acetamido]penicillanic acid:

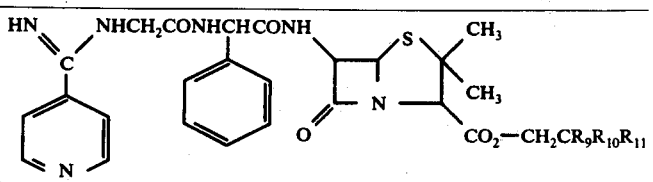

| R_9 | R_10 | R_11 |
|---|---|---|
| Cl | H | H |
| I | H | H |
| Cl | Cl | H |
| Cl | Br | H |
| Br | I | H |
| Cl | Br | Br |
| Cl | Cl | Br |
| Cl | I | H |
| Cl | Cl | I |
| Br | Br | H |
| Br | Br | Br |

EXAMPLE 17

The procedure of Example 13 is repeated. One gram of the intermediate 6-[D-2-(4-pyridylformimidoylaminoacetamido)acetamido]penicillanic acid, p-methoxybenzyl ester hydrochloride in 10 ml. of water and 20 ml. of dimethylformamide is treated with 2 g. of 10% palladium on charcoal and the resulting mixture shaken in a hydrogen atmosphere at atmosheric pressure. After the theoretical amount of hydrogen is absorbed, the spent catalyt is filtered and the filtrate adjusted to pH 5.5 and diluted with 100 ml. of methanol. After crystallization, there is obtained 6-[D-2-phenyl-2-(4-pyridylformimidoylaminoacetamido)acetamido]-penicillanic acid, identical with that prepared in Example 1.

In a similar manner, the intermediate ester products of Example 14 are hydrogenated to give the desired product, 6-[D-2-phenyl-2-(4-pyridylformimidoylaminoacetamido)acetamido]penicillanic acid.

EXAMPLE 18

To 50 ml. of dimethylformamide in a dry round-bottom flask is added 3.12 g. of 4-pyridylformimidoylglycyl-D-phenylglycine. The resulting solution is cooled to −15° C. and treated with 1.08 g. of ethyl chloroformate. This reaction mixture is allowed to stir in the cold for 15 min.

6-Aminopenicillanic acid (2.25 g.) is slurried in 20 ml. of dimethylformamide and treated with 1.08 g. of chlorotrimethylsilane. To the resulting solution is added 1.01 g. of triethylamine, resulting in a precipitate of triethylamine hydrochloride. The mixture is cooled to −10° C. and added to the solution of the mixed anhydride. The resulting reaction is further cooled to −25° C. and allowed to stir for 1 hour. The red solution is allowed to warm to room temperature over a 2 hr. period.

Water (20 ml.) is added to the reaction mixture and the volume concentrated in vacuo to ⅓ to ½, and the residual solution treated with 300 ml. of methanol. The diluted solution is filtered and the filtrate allowed to stir overnight (21 hrs.). The crystallized 6-[D-2-phenyl-2-(4-pyridylformimidoylaminoacetamido)acetamido]-penicillanic acid is filtered and dried, 2.24 g. It is identical with the product from Example 1 in all respects.

In a manner similar to Example 18, 4-pyridylformimidoylglycyl-D-phenylglycine ethoxyformic anhydride can be replaced by the corresponding methoxyformic, i-propoxyformic and pivalic anhydrides with comparable results.

EXAMPLE 19

To a slurry of 3.12 g. of 4-pyridylformimidoylglycyl-d-phenylglycine in 40 ml. of dimethylformamide cooled to −20° C. is added 1.0 g. of N-methylmorpholine followed by 1.2 g. of thionyl chloride. The resulting clear solution is stirred for 45 min. at −15° to −20° C., and is subsequently treated with 2.16 g. of 6-aminopenicillanic acid in 20 ml. of water, 10 ml. of dimethylformamide at pH 7.8. After allowing the reaction mixture to stir for 10 min. at −10° C., it is allowed to warm to room temperature. High-pressure-liquid-chromatography of the solution indicates a yield of 335 mg. of 6-[D-2-phenyl-2-(4-pyridylformimidoylaminoacetamido)acetamido]penicillanic acid (6.5% yield).

EXAMPLE 20

The procedure of Example 19 is repeated for the preparation of 4-pyridylformimidoylglycyl-D-phenylglycyl chloride. The 6-aminopenicillanic acid is replaced by the addition of the indicated 6-aminopenicillanic acid derivative, and the reaction is conducted under the conditions of the indicated example to provide the desired product 6-[D-2-phenyl-2-(4-pyridylformimidoylaminoacetamido)acetamido]penicillanic acid.

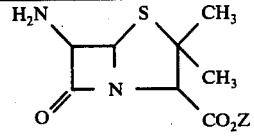

| Z | Reaction Conditions Example # |
|---|---|
| $(CH_3O)_2P-$ | 3 |
| $(n-C_3H_7)_2P-$ | 3 |
| $(C_6H_5)_2P-$ | 3 |
| $3',5'-(t-C_4H_9)_2-4-HOC_6H_2CH_2-$ | 5B |
| $C_6H_5COCH_2-$ | 7 |
| $CH_3COCH_2-$ | 7 |
| $NCCH_2-$ | 7 |
| $CH_3O_2CCH_2-$ | 7 |
| $CH_3CH_2COCH_2-$ | 7 |
| $(CH_3)_2CHCOCH_2-$ | 7 |
| $CH_3(CH_2)_2O_2CCH_2-$ | 7 |
| $C_6H_5CH=N-$ | 9 |
| $CH_3CH=N-$ | 9 |
| $C_2H_5CH=N-$ | 9 |
| $n-C_3H_7CH=N-$ | 9 |
| $(n-C_4H_9)_3Sn-$ | 11 |
| $(CH_3)_3Sn-$ | 11 |
| $(C_2H_5)_3Sn-$ | 11 |
| $(i-C_4H_9)_3Sn-$ | 11 |
| $(s-C_4H_9)_3Sn-$ | 11 |
| $(n-C_3H_7)_3Sn-$ | 11 |
| $p-CH_3OC_6H_4CH_2-$ | 13 |
| $(CH_3)_3C-$ | 13 |
| $p-CH_3OC_6H_4C(CH_3)_2-$ | 13 |
| $p-O_2NC_6H_4CH_2-$ | 13 |
| $(C_6H_5)_2CH-$ | 13 |
| $p-O_2NC_6H_4CH(CH_3)-$ | 13 |
| $CCl_3CH_2-$ | 15 |
| $ICH_2CH_2-$ | 15 |
| $Br_3CCH_2-$ | 15 |
| $Br_2CHCH_2-$ | 15 |

EXAMPLE 21

To a suspension of 3.12 g. of 4-pyridylformimidoylglycyl-D-phenylglycine in 40 ml. of 1-methyl-2-pyrrolidone cooled to −20° C. is added 1.0 g. of N-methylmorpholine followed by 1.2 g. of thionyl chloride. The resulting clear solution is allowed to stir at −15° to −20° C. for 45 min.

6-Aminopenicillanic acid (2.25 g.) is slurried in 20 ml. of 1-methyl-2-pyrrolidone and treated with 1.08 g. of chloro trimethylsilane. To the resulting solution is added 1.01 g. of triethylamine, resulting in a precipitate of triethylamine hydrochloride. The mixture is cooled to −10° C. and added to the solution of the 4-pyridylformimidoylglycyl-D-phenylglycyl chloride. The resulting reaction mixture is further cooled to −25° C. and allowed to stir for 1 hour, and then allowed to warm to room temperature.

Water (20 ml.) is added and the volume of the hydrolyzed mixture reduced in vacuo to ½. The residual solution is treated with 300 ml. of methanol. The precipitated 6-[D-2-phenyl-2-(4-pyridylformimidoylaminoacetamido)acetamido]penicillanic acid, which is filtered and dried, is identical to the product of Example 1.

EXAMPLE 22

A solution of 3.12 g. of 4-pyridylformimidoylglycyl-D-phenylglycine in 30 ml. of dimethylformamide is cooled to −15° C. and treated with 1.18 g. of ethyl chloroformate. After stirring for 15 min. 1.15 g. of N-hydroxysuccinimide is added and the solution allowed to warm to room temperature. The reaction mixture is diluted with 60 ml. of diethyl ether, and the N-hydroxysuccinimide ester hydrochloride allowed to crystallize. The intermediate product is filtered and washed with cold ether.

A solution of 3.5 g. of ester hydrochloride in 40 ml. of dimethylformamide is treated with 2.16 g. of 6-aminopenicillanic acid, and the resulting slurry treated with 850 mg. of pyridine. The reaction mixture is stirred at −10° C. for 30 min. and then allowed to stir at room temperature for 2 hrs. The reaction is diluted with 200 ml. of methanol and the pH adjusted to 5.5 with dilute hydrochloric acid. The resulting precipitate, which is filtered and dried in vacuo, is identical with the product of Example 1.

EXAMPLE 23

A solution of 3.12 g. of 4-pyridylformimidoylglycyl-D-phenylglycine in 40 ml. of dimethylformamide is treated with 1.35 g. of 1-hydroxybenzotriazole, followed by 2.10 g. of dicyclohexylcarbodiimide. The solution is cooled to 0° C. and 2.16 g. of 6-aminopenicillanic acid and 1.1 g. of triethylamine in 25 ml. of dimethylformamide is added. The reaction mixture is allowed to stir for 1 hour in the cold and then allowed to warm to room temperature. After stirring at room temperature for 1 hour, the mixture is hydrolyzed with 50 ml. of water. The precipitated urea is filtered and the filtrate diluted with 200 ml. of methanol. The solution is adjusted to pH 5.5 with dilute hydrochloric acid, and the precipitate which forms on standing a filtered and dried in vacuo. The product is identical to that formed in Example 1.

EXAMPLE 24

To 3.12 g. of 4-pyridylformimidoylglycyl-D-phenylglycine in 30 ml. of 1-methyl-2-pyrrolidone cooled to −15° C. is added 1.18 g. of ethyl chloroformate. After stirring in the cold for 15 min., 1.8 g. of N-hydroxyphthalimide is added and the solution allowed to warm to room temperature. Diethyl ether (60 ml.) is added, and the precipitated ester hydrochloride intermediate is filtered and dried.

A solution of the ester hydrochloride (4.57 g.) in 45 ml. of 1-methyl-2-pyrrolidone cooled to 0° C. is treated with 2.16 g. of 6-aminopenicillanic acid and 850 mg. of pyridine. The mixture is stirred in the cold for 1 hour and then gradually allowed to warm to room temperature. After 30 min. the pH is adjusted to 5.5 and the solution diluted with 225 ml. of methanol. The product, which is filtered and dried in vacuo, is the same as that isolated in Example 1.

EXAMPLE 25

The 4-pyridylformimidoylglycyl-D-phenylglycine derivative employed and isolated in Examples 22, 23 and 24 are prepared and couped with the following 6-aminopenicillanic acid derivatives, employing the reaction conditions of the indicated example to give the product of Example 1:

| Z | Reaction Conditions Example # |
|---|---|
| $(CH_3O)_2P-$ | 3 |
| $(n-C_3H_7)_2P-$ | 3 |
| $(C_6H_5)_2P-$ | 3 |
| $3',5'-(t-C_4H_9)_2-4'-HOC_6H_2CH_2-$ | 5B |
| $C_6H_5COCH_2-$ | 7 |
| $CH_3COCH_2-$ | 7 |
| $NCCH_2-$ | 7 |
| $CH_3O_2CCH_2-$ | 7 |
| $CH_3CH_2COCH_2-$ | 7 |
| $(CH_3)_2CHCOCH_2-$ | 7 |
| $CH_3(CH_2)_2O_2CCH_2-$ | 7 |
| $C_6H_5CH=N-$ | 9 |
| $CH_3CH=N-$ | 9 |
| $C_2H_5CH=N-$ | 9 |
| $n-C_3H_7CH=N=$ | 9 |
| $(n-C_4H_9)_3Sn-$ | 11 |
| $(CH_3)_3Sn-$ | 11 |
| $(C_2H_5)_3Sn-$ | 11 |
| $(i-C_4H_9)_3Sn-$ | 11 |
| $(s-C_4H_9)_3Sn-$ | 11 |
| $(n-C_3H_7)_3Sn-$ | 11 |
| $p-CH_3OC_6H_4CH_2-$ | 13 |
| $(CH_3)_3C-$ | 13 |
| $p-CH_3OC_6H_4C(CH_3)_2-$ | 13 |
| $p-O_2NC_6H_4CH_2-$ | 13 |
| $(C_6H_5)_2CH-$ | 13 |
| $p-O_2NC_6H_4CH(CH_3)-$ | 13 |
| $CCl_3CH_2-$ | 15 |
| $ICH_2CH_2-$ | 15 |
| $Br_3CCH_2-$ | 15 |
| $Br_2CHCH_2-$ | 15 |

EXAMPLE 26

To a slurry of 2.25 g. of 6-aminopenicillanic acid in 20 ml. of dimethylformamide is added 1.08 g. of chloro trimethylsilane followed by 1.01 g. of triethyl amine. The reaction mixture is cooled to −10° C. and 3.5 g. of 4-pyridylformimidoylglycyl-D-phenylglycine N-hydroxysuccinimide ester hydrochloride, prepared by the procedure of Example 22, in 35 ml. of dimethylformamide is added. The resulting reaction mixture is further cooled to −20° C. and allowed to stir for 2 hrs., and is then stirred at room temperature for 1 hour.

Water (20 ml.) is added to the reaction mixture and to volume reduced under reduced pressure to ⅓. The residual solution is treated with 300 ml. of methanol, and the precipitated product filtered and dried. The 6-[D-2-phenyl-2-(4-pyridylformimidoylaminoacetamido)acetamido]penicillanic is identical to that of Example 1.

In a similar manner, the 1-hydroxybenzotriazole and N-hydroxyphthalimide esters of 4-pyridylformimidoylglycyl-D-phenylglycine, prepared in Examples 23 and 24, respectively, can be substituted for the N-hydroxysuccinimide of the present example with similar results.

EXAMPLE 27

To a cooled (0° C.) solution of 5.04 g. of tri-n-butyltin 6-aminopenicillinate and 3.12 g. of 4-pyridylformimidoylglycyl-D-phenylglycine in 50 ml. of dimethylformamide is added 2.10 g. of dicyclohexylcarbodiimide. The mixture is stirred for 1 hour in the cold, and then allowed to warm to room temperature, where it is stirred for an additional 2 hrs. The resulting reaction mixture is then treated with 1.6 g. of potassium thiophenoxide and allowed to stir for 1 hour longer. The mixture is diluted with 20 ml. of water and the pH adjusted to 7.5. The insoluble urea is filtered and the filtrate adjusted to pH 5.5 and diluted with 200 ml. of methanol. The product, which is filtered and dried, is identical with that obtained in Example 1.

Similar results are obtained when N,N-bis(morpholinoethyl)carbodiimide is used in place of dicyclohexylcarbodiimide in the procedure of Example 27.

EXAMPLE 28

Starting with 4-pyridylformimidoylglycyl-D-phenylglycine and either dicyclohexylcarbodiimide or N,N-bis(morpholinoethyl)carbodiimide, the procedure of Example 29 is repeated employing, in place of tri-n-butyltin 6-minopenicillinate, the indicated 6-aminopenicillanic acid derivative and using the work-up procedure of the indicated example, to provide the desired product, 6-[D-2-phenyl-2-(4-pyridylformimidoylaminoacetamido)acetamdo]penicillanic acid.

[structure diagram: penicillanic acid core with $H_2N$, S, $CH_3$, $CH_3$, N, O, $CO_2Z$]

| Z | Reaction Conditions Example # |
|---|---|
| $(CH_3O)_2P-$ | 3 |
| $(n-C_3H_7)_2P-$ | 3 |
| $(C_6H_5)_2P-$ | 3 |
| $3',5'-(t-C_4H_9)_2-4-HOC_6H_2CH_2-$ | 5b |
| $C_6H_5COCH_2-$ | 7 |
| $CH_3COCH_2-$ | 7 |
| $NCCH_2-$ | 7 |
| $CH_3O_2CCH_2-$ | 7 |
| $CH_3CH_2COCH_2-$ | 7 |
| $(CH_3)_2CHCOCH_2-$ | 7 |
| $CH_3(CH_2)_2O_2CCH_2-$ | 7 |
| $C_6H_5CH=N-$ | 9 |
| $CH_3CH=N-$ | 9 |
| $C_2H_5CH=N-$ | 9 |
| $n-C_3H_7CH=N-$ | 9 |
| $(n-C_4H_9)_3Sn-$ | 11 |
| $(CH_3)_3Sn-$ | 11 |
| $(C_2H_5)_3Sn-$ | 11 |
| $(i-C_4H_9)_3Sn-$ | 11 |
| $(s-C_4H_9)_3Sn-$ | 11 |
| $(n-C_3H_7)_3Sn-$ | 11 |
| $p-CH_3OC_6H_4CH_2-$ | 13 |
| $(CH_3)_3C-$ | 13 |
| $p-CH_3OC_6H_4C(CH_3)_2-$ | 13 |
| $p-O_2NC_6H_4CH_2-$ | 13 |
| $(C_6H_5)_2CH-$ | 13 |
| $p-O_2NC_6H_4CH(CH_3)-$ | 13 |
| $CCl_3CH_2-$ | 15 |
| $ICH_2CH_2-$ | 15 |
| $Br_3CCH_2-$ | 15 |
| $Br_2CHCH_2-$ | 15 |
| $H-$ | 1 |

EXAMPLE 29

To a slurry of 2.25 g. of 6-aminopenicillanic acid in 20 ml. of dimethylformamide is added 1.08 g. of chloro trimethylsilane followed by 1.01 g. of triethyl amine. The reaction mixture is cooled to $-10°$ C. and 3.12 g. of 4-pyridylformimidoylglycyl-D-phenylglycine and 2.1 g. of dicyclohexylcarbodiimide in 35 ml. of dimethyl-formamide is added. The resulting reaction mixture is further cooled to $-20°$ C. and allowed to stir for 2 hrs., and is then stirred at room temperature for 1 hour.

Water (20 ml.) is added to the reaction mixture, the precipitated dicyclohexylurea is filtered and the volume reduced under reduce pressure to ⅓. The residual solution is treated with 300 ml. of methanol, and the precipitated product filtered and dried. The 6-[D-2-phenyl-2-(4-pyridylformimidoylaminoacetamido)acetamido]-penicillanic is identical to that of Example 1.

In a similar manner, N,N-bis(morpholinoethyl)carbodiimide can be substituted for the dicyclohexylcarbodiimide of the present example with similar results.

EXAMPLE 30

A solution of 3.12 g. of 4-pyridylformimidoylglycyl-D-phenylglycine in 40 ml. of dimethylformamide is treated with 1.39 g. of p-nitrophenol, followed by 2.10 g. of dicyclohexylcarbodiimide. The solution is cooled to 0° C. and 2.16 g. of 6-aminopenicillanic acid and 1.1 g. of triethylamine in 25 ml. of dimethylformamide is added. The reaction mixture is allowed to stir for one hour in the cold and then allowed to warm to room temperature. After stirring at room temperature for one hour, the precipitated dicyclohexylurea is filtered and the mixture is diluted with 200 ml. of methanol. The solution is adjusted to pH 5.5 with dilute hydrochloric acid, and the precipitate which forms on standing is filtered and dried in vacuo. The product is identical to that formed in Example 1.

EXAMPLE 31

That portion of the procedure of Example 30 for the preparation of the 4-pyridylformimidoylglycyl-D-phenylglycine ester is repeated employing the appropriate phenol or thiophenol indicated. This ester is coupled with the requisite 6-aminopenicillanic acid derivative under the acylation and work-up conditions of the indicated example to give the desired product, 6-[D-2-phenyl-2-(4-pyridylformimidoylaminoacetamido)acetamido]penicillanic acid.

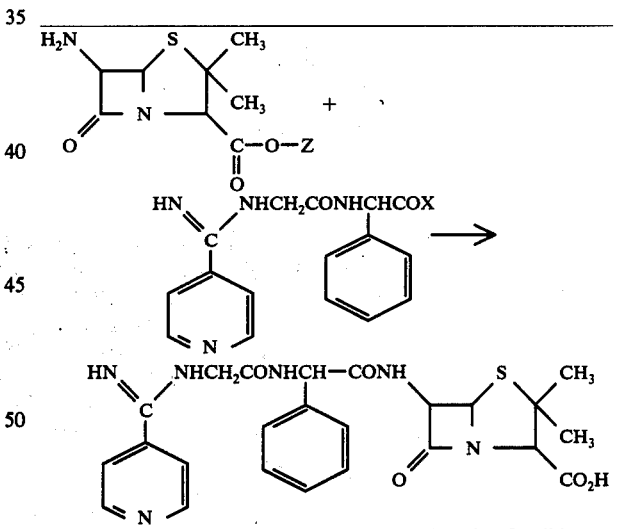

| Z | X | Reaction Conditions Example # |
|---|---|---|
| $(CH_3O)_2P-$ | $C_6H_5O-$ | 3 |
| $(CH_3O)_2P-$ | $2-C_5H_4NS-$ | 3 |
| $(n-C_3H_7)_2P-$ | $4-ClC_6H_4O-$ | 3 |
| $(C_6H_5)_2P-$ | $4-ClC_6H_4S-$ | 3 |
| $(C_6H_5)_2P-$ | $4-NO_2C_6H_4S-$ | 3 |
| $3',5'-(t-C_4H_9)_2-$ $4-HOC_6H_2CH_2-$ | $4-ClC_6H_4O-$ | 5B |
| $C_6H_5COCH_2-$ | $C_6H_5O-$ | 7 |
| $C_6H_5COCH_2-$ | $4-NO_2C_6H_4S-$ | 7 |
| $CH_3COCH_2-$ | $4-NO_2C_6H_4S-$ | 7 |
| $CH_3COCH_2-$ | $2-C_5H_4NS-$ | 7 |
| $CH_3COCH_2-$ | $4-NO_2C_6H_4O-$ | 7 |
| $NCCH_2-$ | $4-NO_2C_6H_4O-$ | 7 |
| $CH_3O_2CCH_2-$ | $C_6H_5S-$ | 7 |
| $CH_3O_2CCH_2-$ | $2-C_5H_4NS-$ | 7 |
| $CH_3CH_2COCH_2-$ | $4-ClC_6H_4O-$ | 7 |
| $CH_3CH_2COCH_2-$ | $4-ClC_6H_4S-$ | 7 |
| $(CH_3)_2CHCOCH_2-$ | $4-ClC_6H_4S-$ | 7 |

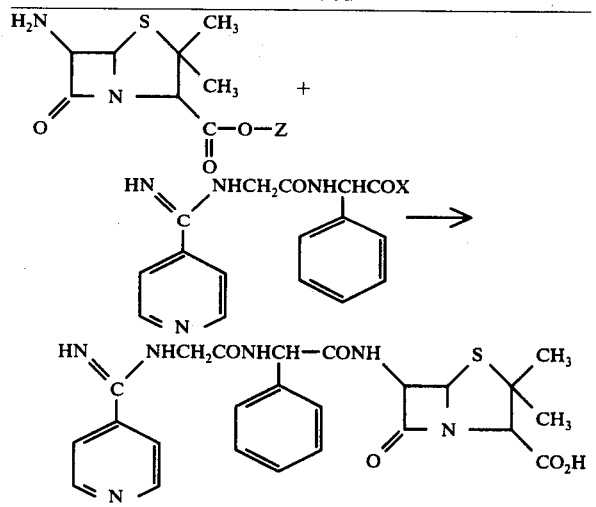

| Z | X | Reaction Conditions Example # |
|---|---|---|
| (CH₃)₂CHCOCH₂— | 4-NO₂C₆H₄O— | 7 |
| CH₃(CH₂)₂O₂CCH₂— | C₆H₅O— | 7 |
| CH₃(CH₂)₂O₂CCH₂— | C₆H₅S— | 7 |
| C₆H₅CH=N— | C₆H₅S— | 9 |
| C₂H₅CH=N— | 4-ClC₆H₄S— | 9 |
| C₂H₅CH=N— | 4-NO₂C₆H₄O— | 9 |
| (n-C₄H₉)₃Sn— | 4-ClC₆H₄O— | 11 |
| (CH₃)₃Sn— | 4-ClC₆H₄O— | 11 |
| (i-C₄H₉)₃Sn— | C₆H₅S— | 11 |
| (n-C₃H₇)₃Sn— | C₆H₅S— | 11 |
| (n-C₃H₇)₃Sn— | C₆H₅O— | 11 |
| p-CH₃OC₆H₄CH₂— | 4-ClC₆H₄S— | 13 |
| p-CH₃OC₆H₄CH₂— | 2-C₄H₄NS— | 13 |
| (CH₃)₃C— | 4-NO₂C₆H₄O— | 13 |
| p-CH₃OC₆H₄C(CH₃)₂— | 4-ClC₆H₄S— | 13 |
| p-NO₂C₆H₄CH₂— | 4-NO₂C₆H₄O— | 13 |
| (C₆H₅)₂CH— | C₆H₅O— | 13 |
| p-NO₂C₆H₄CH(CH₃)— | C₆H₅O— | 13 |
| CCl₃CH₂— | 4-ClC₆H₄O— | 15 |
| CCl₃CH₂— | 4-ClC₆H₄S— | 15 |
| CCl₃CH₂— | 4-NO₂C₆H₄S— | 15 |
| ICH₂CH₂— | C₆H₅O— | 15 |
| Br₃CCH₂— | 2-C₄H₄NS— | 15 |
| Br₂CHCH₂— | 4-ClC₆H₄O— | 15 |

EXAMPLE 32

To a slurry of 4.5 g. of 6-aminopenicillanic acid in 40 ml. of dimethylformamide is added 1.28 g. of dichloro dimethylsilane followed by 2.02 g. of triethyl amine. The reaction mixture is cooled to −10° C. and 7.0 g. of 4-pyridylformimidoylglycyl-D-phenylglycine N-hydroxysuccinimide ester hydrochloride, prepared by the procedure of Example 22, in 70 ml. of dimethylformamide is added. The resulting reaction mixture is further cooled to −20° C. and allowed to stir for 2 hrs., and is then stirred at room temperature for 1 hour.

Water (40 ml.) is added to the reaction mixture and to volume reduced under reduced pressure to ⅓. The residual solution is treated with 600 ml. of methanol, and the precipitated product filtered and dried. The 6-[D-2-phenyl-2-(4-pyridylformimidoylaminoacetamido)acetamido]penicillanic is identical to that of Example 1.

EXAMPLE 33

A suspension of 4.2 g. of 6-aminopenicillanic acid saccharimide hydrochloride in 50 ml. of dimethylformamide is treated with 1.01 g. of triethylamine and the solution cooled to −5° C. To this solution is added 4-pyridylformimidoylglycyl-D-phenylglycine ethoxyformic anhydride as prepared in Example 5A over a period of 5 minutes. The reaction mixture is allowed to stir in the cold for 30 minutes, and is then treated with 840 mg. of sodium bicarbonate in 10 ml. of water. After stirring at room temperature, the reaction pH is adjusted to 5.5 with dilute hydrochloric acid. The volume of the reaction is concentrated in vacuo to about 60 ml. and 200 ml. of methanol is added. The precipitate which forms on standing is filtered and dried to give 6-[D-2-phenyl-2-(4-pyridylformimidoylaminoacetamido)acetamido]penicillanic acid, identical to that from Example 1.

EXAMPLE 34

The procedure of Example 33 is repeated, substituting for 4-pyridylformimidoylglycyl-D-phenylglycine ethoxyformic anhydride the following mixed anhydride prepared from Examples 2 and 4, to give the desired product, 6-[D-2-phenyl-2-(4-pyridylformimidoylaminoacetamido)acetamido]penicillanic acid:

4-pyridylformimidoylglycyl-D-phenylglycine pivalic anhydride;

4-pyridylformimidoylglycyl-D-phenylglycine methoxyformic anhydride;

4-pyridylformimidoylglycyl-D-phenylglycine i-propoxyformic anhydride; and 4-pyridylformimidoylglycyl-D-phenylglycine n-butoxyformic anhydride.

EXAMPLE 35

To a slurry of 3.12 g. of 4-pyridylformimidoylglycyl-D-phenylglycine in 40 ml. of dimethylformamide cooled to −20° C. is added 1.0 g. of N-methylmorpholine followed by 1.2 g. of thionyl chloride. The resulting solution is allowed to stir for 45 minutes at −15° to −20° C., and is then allowed to warm to −5° C.

A suspension of 4.2 g of 6-aminopenicillanic acid saccharimide hydrochloride in 50 ml. of dimethylformamide is treated with 1.01 g. of triethylamine, cooled to −5° C. and added over a 5 minute period to the above acid chloride. The resulting reaction mixture is allowed to stir at −5° C. for 30 minutes. Sodium bicarbonate (840 mg.) in 10 ml. of water is added to the reaction mixture and the resulting solution allowed to stir at room temperature for 3 hours. The pH is adjusted to 5.5 by the addition of dilute hydrochloric acid and, the volume of the solution concentrated under reduced pressure to about 60 ml. Methanol (200 ml.) is added and the solution allowed to stand at room temperature until crystallization ceases. The product, which is filtered and dried, is identical with the product of Example 1.

EXAMPLE 36

A solution of 3.5 g. of 4-pyridylformimidoylglycyl-D-phenylglycine N-hydroxysuccinimide ester hydrochloride, prepared by the procedure of Example 22, in 40 ml. of dimethylformamide is treated with 4.2 g. of 6-aminopenicillanic acid saccharimide hydrochloride, cooled to −5° C. and the resulting slurry treated with 1.7 g. of pyridine. Stirring in the cold is continued for 45 minutes, followed by the addition of 840 mg. of sodium bicarbonate in 10 ml. of water. After stirring at room temperature for 3 hours, the pH is adjusted to 5.5 with dilute hydrochloric acid and 200 ml. of methanol is added. On standing, the product crystallizes and is subsequently filtered and dried. The product, 6-[D-2-phenyl-2-(4-pyridylformimidoylaminoacetamido)acetamido]-penicillanic acid is identical with that formed in Example 1.

EXAMPLE 37

A solution of 3.12 g. of 4-pyridylformimidoylglycyl-D-phenylglycine in 40 ml. of dimethylformamide is treated with 1.35 g. of 1-hydroxybenzotriazole, followed by 2.10 g. of dicyclohexylcarbodiimide. The solution is cooled to −5° C. and 4.2 g. of 6-aminopenicillanic acid saccharimide hydrochloride and 1.1 g. of triethylamine in 25 ml. of dimethylformamide is added. The reaction mixture is allowed to stir for 1 hour in the cold and then allowed to warm to room temperature. Sodium bicarbonate (840 mg.) in 30 ml. of water is added and the reaction mixture allowed to stir for 3 hours. The precipitated dicyclohexylurea is filtered and the filtrate adjusted to a pH of 5.5. Following concentration in vacuo to about 50 ml., 200 ml. of methanol is added, and the solution allowed to stand at room temperature. The product, after filtration and drying, proved to be identical to the 6-[D-2-phenyl-2-(4-pyridylformimidoylaminoacetamido)acetamido]penicillanic acid of Example 1.

EXAMPLE 38

A solution of 4.57 g. of 4-pyridylformimidoylglycyl-D-phenylglycine N-hydroxyphthalimide ester hydrochloride, prepared according to the procedure of Example 24, in 45 ml. of 1-methyl-2-pyrrolidone cooled to −5° C. is treated with 4.2 g. of 4-aminopenicillanic acid saccharimide hydrochloride followed by 850 mg. of pyridine. After stirring at −5° C. for 45 minutes, the mixture is allowed to warm to room temperature. Sodium bicarbonate (840 mg.) in 10 ml. of water is added and the reaction mixture allowed to stir for an additional 3 hours. The pH is adjusted to 5.5 and 200 ml. of methanol is added. The precipitate which forms, when filtered and dried, is identical to the 6-[D-2-phenyl-2-(4-pyridylformimidoylaminoacetamido)acetamido]penicillanic of Example 1.

EXAMPLE 39

To a cooled (−5° C.) solution of 4.2 g. of 6-aminopenicillanic acid saccharimide hydrochloride, 3.12 g. of 4-pyridylformimidoylglycyl-D-phenylglycine and 1.01 g. of triethylamine in 50 ml. of dimethylformamide is added 2.10 g. of dicyclohexylcarbodiimide, and the reaction mixture allowed to stir in the cold for 45 minutes. The mixture is allowed to warm to room temperature followed by the addition of 840 mg. of sodium bicarbonate in 20 ml. of water. The precipitated dicyclohexylurea is filtered and the filtrate concentrated to about 45 ml. The pH is adjusted to 5.5 and 200 ml. of methanol is added. The product, which is filtered and dried, is identical to the 6-[D-2-phenyl-2(4-pyridylformimidoylaminoacetamido)acetamido]penicillanic acid of Example 1.

EXAMPLE 40

A solution of 3.12 g. of 4-pyridylformimidoylglycyl-D-phenylglycine in 40 ml. of dimethylformamide is treated with 1.39 g. of p-nitrophenol, followed by 2.10 g. of dicyclohexylcarbodiimide. The solution is cooled to −5° C. and 4.2 g. of 6-aminopenicillanic acid saccharimide hydrochloride and 1.1 g. of triethylamine in 25 ml. of dimethylformamide is added. The reaction mixture is allowed to stir for 1 hour in the cold and then allowed to warm to room temperature. After stirring at room temperature for 3 hours with 840 mg. of sodium bicarbonate in 10 ml. of water, the precipitated dicyclohexylurea is filtered and the mixture is diluted with 200 ml. of methanol. The solution is adjusted to pH 5.5 with dilute hydrochloric acid and the precipitate which forms on standing is filtered and dried in vacuo. The product is identical to that formed in Example 1.

EXAMPLE 41

That portion of the procedure of Example 40 for the preparation of the 4-pyridylformimidoylglycyl-D-phenylglycine ester is repeated employing the appropriate phenol or thiophenol indicated. This ester is coupled with the requisite 6-aminopenicillanic acid saccharimide derivative under the acylation and work-up conditions indicated to give the desired product, 6-[D-2-phenyl-2-(4-pyridylformimidoylaminoacetamido)acetamido]penicillanic acid.

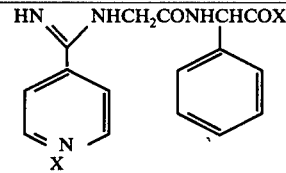

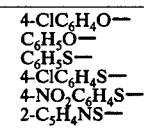

4-ClC$_6$H$_4$O—
C$_6$H$_5$O—
C$_6$H$_5$S—
4-ClC$_6$H$_4$S—
4-NO$_2$C$_6$H$_4$S—
2-C$_5$H$_4$NS—

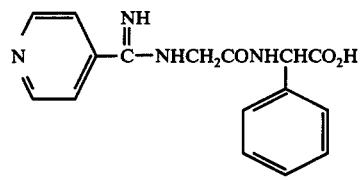

What is claimed is:
1. The compound, 4-pyridylformimidoylglycyl-D-phenylglycine, of the formula: